United States Patent [19]

Waggener et al.

[11] Patent Number: 5,573,732

[45] Date of Patent: Nov. 12, 1996

[54] METHOD AND APPARATUS FOR STERILIZING MEDICAL DEVICES USING GLOW DISCHARGES

[75] Inventors: Herbert A. Waggener, Pottersville; Kazimierz Przydzial, Clark, both of N.J.

[73] Assignee: Waggener, Przydzial and Associates, Chippewa Falls, Wis.

[21] Appl. No.: 302,621

[22] Filed: Sep. 8, 1994

[51] Int. Cl.⁶ .................................................. B01J 19/08
[52] U.S. Cl. ........................ 422/186.06; 422/22; 422/907
[58] Field of Search ........................... 422/22, 186.06, 422/907

[56] References Cited

U.S. PATENT DOCUMENTS

| | | | |
|---|---|---|---|
| 2,509,258 | 5/1950 | Wing | 21/54 |
| 3,481,266 | 12/1969 | Püschner | 99/253 |
| 3,831,052 | 8/1974 | Knechtli | 313/187 |
| 4,040,388 | 8/1977 | Miller | 119/1 |
| 4,051,044 | 9/1977 | Sörensen | 250/531 |
| 4,080,578 | 3/1978 | Farish et al. | 331/94.5 |
| 4,458,153 | 7/1984 | Wesley | 250/435 |
| 4,458,630 | 7/1984 | Shatma | 119/1 |
| 4,469,047 | 9/1984 | Miller | 119/1 |
| 4,593,646 | 6/1986 | Miller et al. | 119/1 |
| 4,681,063 | 7/1987 | Hebrank | 119/1 |
| 4,896,073 | 1/1990 | Maitland et al. | 313/634 |
| 4,903,635 | 2/1990 | Hebrank | 119/1 |
| 4,909,995 | 3/1990 | Jacob | 422/186.29 |
| 4,986,906 | 1/1991 | Dadisman | 210/169 |
| 5,056,464 | 10/1991 | Lewis | 119/6.8 |
| 5,120,512 | 6/1992 | Masuda | 422/297 |
| 5,136,979 | 8/1992 | Paul et al. | 119/6.8 |
| 5,145,640 | 9/1992 | Levin | 422/22 |
| 5,148,004 | 9/1992 | Gettig et al. | 219/390 |
| 5,158,038 | 10/1992 | Sheeks et al. | 119/6.8 |
| 5,176,101 | 1/1993 | Paul et al. | 119/6.8 |
| 5,190,703 | 3/1993 | Rose et al. | 264/22 |

Primary Examiner—Charles T. Jordan
Assistant Examiner—Daniel Jenkins
Attorney, Agent, or Firm—Irwin Ostroff; Erwin W. Pfeifle

[57] ABSTRACT

A medical device having a regular or irregular shape is sterilized in a sterilizing apparatus comprising a means for moveably supporting the medical device, and a electrode having an anode tip at one end thereof which is positioned to form a gap with a predetermined length between the anode tip and the medical device. To sterilize a portion of an outer surface of the medical device at the anode tip of the electrode, predetermined first and second voltages are applied to the anode tip and the medical device, respectively. The voltage and current applied to the anode tip and the medical device are raised to predetermined values to provide a voltage differential across the gap to form a glow discharge adjacent the outer surface of the medical device for sterilizing the outer surface of the medical device. The entire outer surface around the medical device is sterilized by, for example, positioning a plurality of energized electrodes around the medical device to form a continuous band of glow discharges around the medical device. A length of the medical device can be sterilized by moving the medical device and the anode tips of the electrodes relative to each other while forming a sequence of overlapping glow discharges both along a predetermined length and around the outer surface of the medical device.

29 Claims, 7 Drawing Sheets

METHOD AND APPARATUS FOR STERILIZING MEDICAL DEVICES USING GLOW DISCHARGES

CROSS REFERENCE TO RELATED APPLICATIONS

This application is related to another patent application entitled "OZONE GENERATORS USING GLOW DISCHARGES", in which the assignee and the inventorship are the same as the present application and which is being filed concurrently with the present application.

1. Field of the Invention

The present invention relates to method and apparatus for sterilizing medical-type devices such as injection needles, dental burrs, surgical knives, eye pressure measuring devices, etc. that have a substantially regular shape.

2. Background of the Invention

Numerous methods and apparatus are known for sterilizing devices that are repeatedly used in medical fields such as by doctors, dentists, and optometrists, and in various other fields such as for egg inoculation. For example, typical devices which need to be sterilized between each use or before disposal are, for example, surgical knives, dental burrs, eye pressure measuring devices, and injection needles used, for example, for human use or for inoculating eggs against infectious diseases or introducing growth hormones.

U.S. Pat. No. 4,909,995 (A. Jacob), issued on Mar. 20, 1990, discloses a process for the dry sterilization of medical devices and materials in which the materials are placed in a chamber which is evacuated to a sub-atmospheric pressure and provided with a flow of a predetermined gas. Radio Frequency (RF) energy is applied to the gas in the chamber to create a plasma containing a number of excited species of molecules and atoms. The excited species of molecules and atoms interact with the surface of the materials to sterilize it. The time duration needed for the sterilization process depends on the amount of gas flow in the chamber, the pressure, the RF power density, and the load (materials) size.

U.S. Pat. No. 5,148,004 (W. Gettig et al.), issued on Sep. 15, 1992, discloses a method and apparatus for sterilizing contaminated syringe needles prior to their disposal to avoid accidental exposure or infection of others by a virus or disease found in bioburden existing on the used needles. The apparatus comprises an elongated heating tube having a central bore capable of receiving the needle of a syringe assembly which is heated by an electrical resistance material surrounding the tube. Precise control over the interval and level of heating of the tube is provided through a power controller associated with logic circuitry. The concentrated heat applied to the air within the bore of the tube causes the needle to be sterilized, annealed, and have a blackened appearance. This renders the needle physically unusable.

An autoclave is a another well-known sterilizing device for sterilizing medical devices between use. More particularly, the autoclave is a strong, closed, self-regulating vessel similar to a pressure cooker in which steam under pressure provides sterilization. Such device provides excellent sterilization results with confirmation, but requires a reasonable long time period, such as an hour, to reach and maintain the heat and pressure in order achieve sterilization of the medical devices.

Injection needles are used for the inoculation of eggs. It is important to prevent these needles from becoming contaminated from some eggs and then infecting subsequently injected eggs. U.S. Pat. No. 4,593,646 (G. Miller et al.), issued on Jun.10, 1986, discloses egg injection apparatus comprising a plurality of injection needles, heat generating means, and needle cleaning means. More particularly, each needle punctures a separate egg to inject a predetermined liquid, and the heat generating means applies heat for heat sealing the injection hole by solidifying albumin at the hole. The needle cleaning means comprises a wire which is automatically projected through the bore of by the movement of each needle to clean out any remains of the injection process.

U.S. Pat. No. 5,158,038 (O. Sheeks et al.), issued on Oct. 27, 1992, discloses an egg injecting apparatus where the needle and egg shell are sprayed with a disinfectant solution immediately prior to the needle penetrating the egg shell in order to sterilize the egg shell and the needle as the egg is being inoculated.

U.S. Pat. 4,040,388 (G. Miller), issued on Aug. 9, 1977, discloses an egg injecting apparatus wherein eggs are automatically inoculated with an antibiotic solution. The apparatus heat-sterilizes a portion of the shell with a hot shoe, drives a needle through the sterilized portion, injects the solution through the needle, withdraws the needle, heat-coagulates a portion of the egg albumin at the hole with the hot shoe, and heat-sterilizes the needle before inoculating the next egg. The sterilization of the needle is achieved with an electrical heating element which surrounds an upper portion of a tube adjacent the hot shoe and the injecting end of a retracted needle.

It is desirable to provide a non-contact sterilization technique that kills all bacteria on a medical-type device in a very fast and efficient manner, and provides a way of ensuring that the sterilization process is complete.

SUMMARY OF THE INVENTION

The present invention is directed to method and apparatus for sterilizing medical-type devices such as injection needles, dental burrs, surgical knives, eye pressure measuring devices, etc. that have a substantially regular shape using one or more glow discharges.

Viewed from one aspect, the present invention is directed to apparatus for sterilizing an electrically conductive portion of a medical device. The apparatus comprises an electrode, and positioning means. The positioning means positions the electrode at a predetermined distance from the electrically conductive portion of the medical device. The electrode and the conductive portion of the medical device are separated by a gap which is sufficient, with an appropriate potential difference between the electrode and the medical device, to facilitate an electrical path between the electrode and the medical device to produce a glow discharge adjacent the outer surface of the medical device. In this manner the portion of the medical device contacted by the glow discharge is sterilized.

Viewed from another aspect, the present invention is directed to sterilizing apparatus comprising supporting means and an electrode. The supporting means supports a medical device that comprises a substantially regular shape along a section to be sterilized, and selectively applies a predetermined first voltage to the medical device. The electrode comprises an anode tip which is arranged to provide a gap of a predetermined length between an outer surface of the medical device and the anode tip when the anode tip is positioned next to the medical device. The electrode is arranged to selectively receive a predetermined second voltage to provide a predetermined voltage differential across the gap to form a glow discharge adjacent the outer surface of the medical device in the area of the gap for sterilizing the outer surface of the medical device in the area of the glow discharge.

Viewed from still another aspect, the present invention is directed to a method for sterilizing medical devices comprising the following steps. In a first step, a medical device that comprises a substantially regular shape along a section to be sterilized is moveably supported. In a second step, a portion of the medical device to be sterilized is selectively moved adjacent an anode tip at one end of a projection, the anode tip being arranged to provide a gap of a predetermined length between an outer surface of the medical device and the anode tip when the anode tip is positioned next to the medical device. In a third step, a sufficient voltage difference is selectively applied between the anode tip of the electrode and the medical device to form a glow discharge adjacent the outer surface of the medical device in the area of the gap for sterilizing the outer surface of the medical device in the area of the glow discharge.

Viewed from still another aspect, an entire outer surface along a desired length of a medical device can be sterilized by a sterilization device comprising a plurality of electrodes. Each electrode comprises an anode tip at one end thereof which is arranged to provide a gap of a predetermined length between an outer surface of the medical device and the anode tip of the electrode when the anode tip is positioned next to the medical device. To sterilize the desired length of the outer surface of the medical device, a sufficient voltage differential is applied between each of the anode tips and the medical device to form glow discharges. At a predetermined voltage and current in the area of the gap adjacent the outer surface of the medical device, a continuous band of glow discharges are formed which sterilizes the outer surface around the medical device. A series of glow discharges are then formed while the medical device and the anode tips of the electrodes are moved relative to each other until the desired length of the medical device is sterilized by the glow discharges.

The invention will be better understood from the following more detailed description taken with the accompanying drawings and claims.

DETAILED DESCRIPTION

It is to be understood that corresponding elements having the same function in the several views of the drawings are provided with the same designation numbers.

Figure 1:
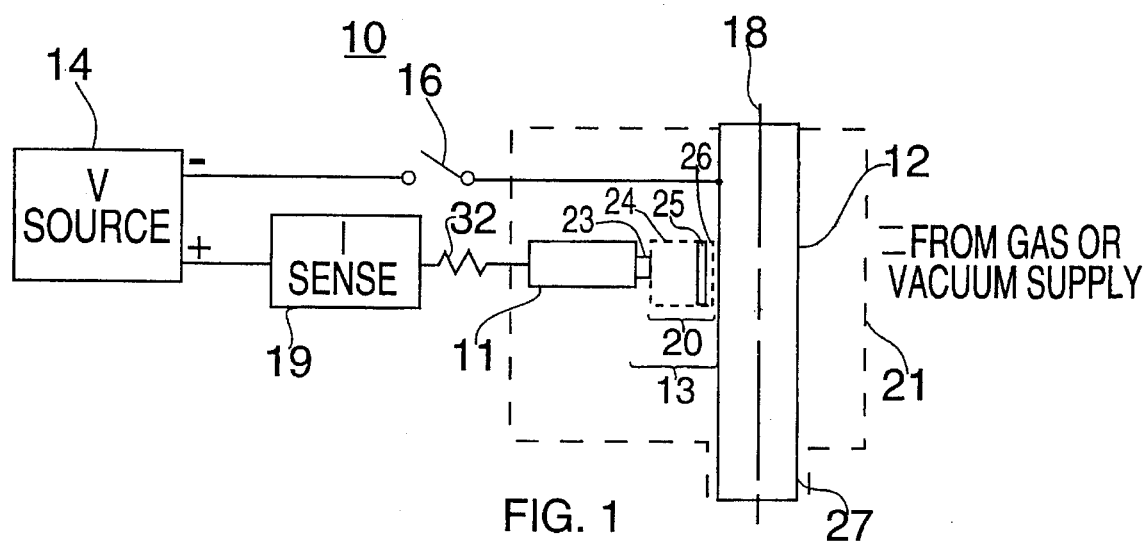
FIG. 1 is a side view of a general device for producing a glow discharge.

Referring now to FIG. 1, there is shown a side view of a typical device 10 for explaining how a glow discharge 20 is formed. The device 10 comprises an anode 11, a cathode 12, a D.C. voltage source (V SOURCE) 14, a switching means 16, a current sensing means (I SENSE) 19, an optional chamber 21 (shown as a dashed line rectangle) which can be supplied with a controlled gas composition and comprises an exit orifice or seal 27 surrounding the cathode 12 at one exit point from the chamber 21, and a ballast resistor 32. More particularly, one end of the anode 11 is positioned near a side surface of the cathode 12 with a gap 13 having a predetermined length therebetween. A serial connection of the D.C. voltage source 14 and the switching means 16 through the ballast resistor 32 electrically couples the anode 11 to the cathode 12. The switching means 16 can comprise any suitable device for closing and opening the connection coupling the anode 11 and the cathode 12 during any desired selective time period. When the switching means 16 is closed, a predetermined voltage ($V_{Source}$) is applied by the D.C. voltage source 14 between the anode 11 and the cathode 12 through the ballast resistor 32 to form the glow discharge 20 adjacent the outer surface of the cathode 12.

The glow discharge 20 has four main sequential regions comprising an anode glow 23 (shown as a solid rectangle) near the anode 11, a relatively non-luminous plasma column (shown as a dashed line rectangle) 24, a cathode glow shown as a solid rectangle) 25, and a cathode dark space (shown as a dashed line rectangle) 26 near the cathode 12. The length of the (fixed) gap is preferably in the order of from 0.5 mil to 6.0 mils in order to use reasonable operating voltages and currents for providing the glow discharge 20. Regarding the regions 23–26 of the glow discharge 20, most of the applied voltage across the gap 13 appears across the cathode dark space 26. This indicates that most of the heat generated is dissipated in the cathode 12. The cathode glow 25 marks the boundary with the cathode dark space 26 and is a visible indication of the lateral extent of the glow discharge 20. The non-luminous plasma column 24 exhibits a relatively low voltage drop and essentially connects the cathode glow 25 to the anode 11. The anode glow 23 is important when conditions in the vicinity of the anode glow region 23 causes reconstruction or growth of the anode 11.

Figure 2:
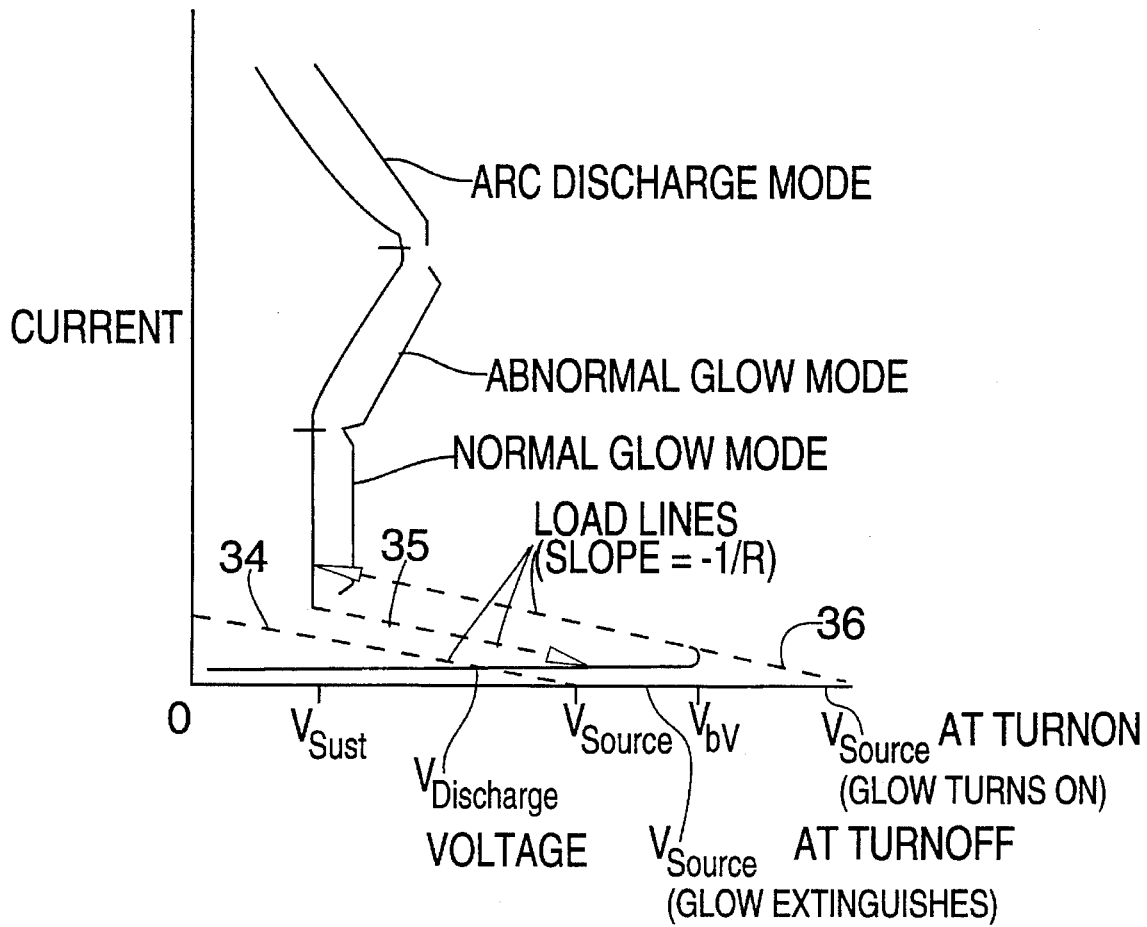
FIG. 2 is a curve of current versus voltage produced during the operation of the device of FIG. 1.

Referring now to FIG. 2, there is shown a curve of current (y-axis) versus voltage (x-axis) for explaining the operation of the device 10 of FIG. 1. With the switching means 16 closed, the D.C. voltage source 14 applies a positive voltage ($V_{Source}$) through the ballast resistor 32 to the anode 11 and a negative voltage to the cathode 12. As the voltage between the anode 11 and the cathode 12 is steadily increased, the anode-cathode voltage steadily increases from zero volts while a small substantially steady current is produced from residual ionization of a gas (e.g., air) in the gap 13 until a breakdown voltage ($V_{bv}$) is reached. This is shown by the exemplary load line 36. When approaching the breakdown voltage value, impact ionization multiplies the number of initial ionizing events in the gas to produce voltage breakdown and form a glow discharge 20 (shown only in FIG. 1)

adjacent the outer surface of the cathode 12 at a Voltage somewhat greater than Vsust. It should be noted that $V_{gap}+iR=V_{Source}$, where $V_{gap}$ is the voltage across the gap 13, $V_{Source}$ is the voltage provided by the voltage source 14, and iR is the product of the instantaneous current and the value of the ballast resistor 32, which is shown by the exemplary load line 36. More particularly, as soon as the gap voltage ($V_{gap}$) exceeds the breakdown voltage ($V_{bV}$), the operating point switches to the Normal/Abnormal Glow Mode region provided that the value (R) of the ballast resistor 32 is sufficiently large to prevent entering the Arc Mode, and providing that the ballast resistor 32 has a resistance value which is not too large so as to keep the gap voltage ($V_{gap}$) less than the break down voltage ($V_{bV}$). If the supply voltage ($V_{Source}$) is now lowered so that the gap voltage is less than $V_{sust}$, the impact ionization falls below that needed to sustain the glow discharge 20 and the current (i) is reduced to a current caused by an initial ionization of the gas in the gap 13. This is shown by the exemplary load line 35. Vsust is at a somewhat lower voltage than $V_{bV}$, and the value of $V_{bV}$ and Vsust are dependent on various parameters such as the materials of the anode 11 and cathode 12, the length of the gap 13, and the pressure and gas found in the gap 13. With, for example, air at atmospheric pressure in the gap 13, many things occur in the glow discharge 20 as, for example, the formation of a combination of ions of oxygen and nitrogen.

Once the sustaining glow discharge 20 has been formed, as the voltage is increased, the voltage remains approximately at $V_{sust}$ during a "Normal Glow Mode" section of the curve while the current is increased. However, as the current increases in the "Normal Glow Mode" section, the glow discharge 20 increases in size or area adjacent the outer surface of the cathode 12. However, at a predetermined current level, the curve obtains a definite positive slope and enters what is called the "Abnormal Glow Mode". As the voltage and current is further increased to a larger predetermined value, an Arc Mode (not shown) is obtained wherein an electrical arc (e.g., used for arc welding) is formed between the anode 11 and cathode 12. The Arc Mode is of no interest to the present invention and will not be discussed further. It is to be understood that the anode 11 and cathode 12 can be placed in an optional chamber 21 (shown only in FIG. 1 as a dashed line rectangle) for introducing a gas at a desired pressure that will sustain a glow discharge 20. For example, the gas can be filtered treated air to prevent particles, organics, and moisture from reaching the gap 13, or a reactive gas such as oxygen or toxic gases such as poisons like carbonyls. It is to be understood that the preferred gas is air at atmospheric pressure. Additionally, the chamber 21 can be used for collecting the residual gases produced by the glow discharges 20, since the residual gases in sufficient quantities may be toxic. Moreover, the chamber 21 forms a means for preventing unwanted access to the regions 23–26 of the glow discharges 20 to increase operator safety. Under some conditions, considerable structural changes occur in the topology of the surface of the anode 11. More particularly, metallic filaments may form on the anodes 11 which have dimensions sufficient to bridge the anode-cathode gap 13 causing an electrical short. Still further, anodes 11 comprising tungsten have been found to eliminate this condition for causing an electrical short, and anodes 11 comprising molybdenum or carbon are also expected to be useful to eliminate this condition.

Figure 3:
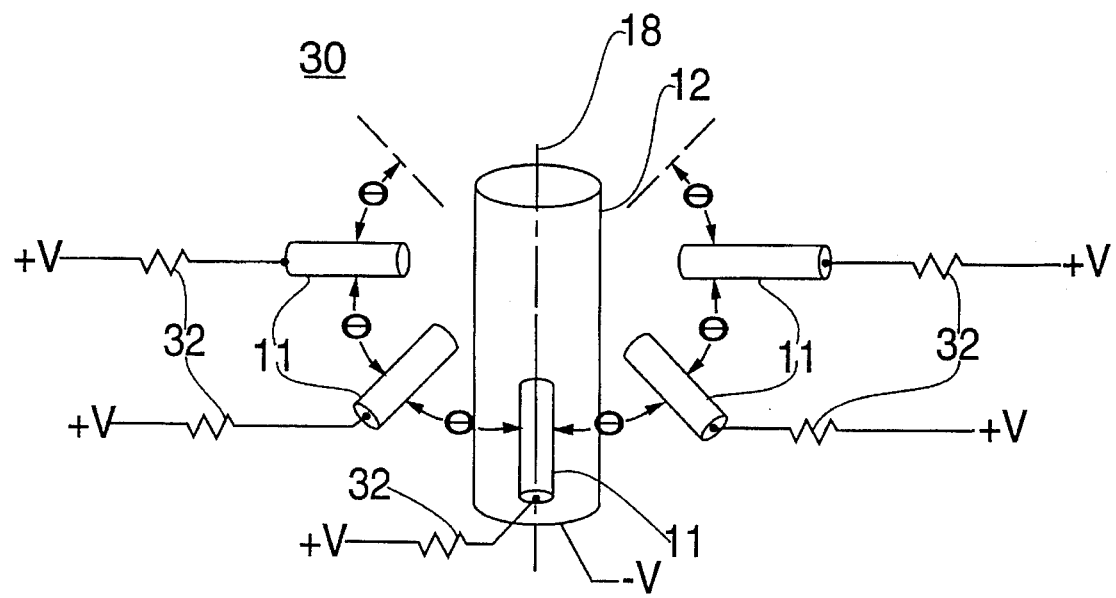
FIG. 3 is a perspective view of a generic apparatus for sterilizing a medical device using a plurality of the devices of FIG. 1 in accordance with the present invention.

Referring now to FIG. 3, there is shown a perspective view of a basic apparatus 30 for sterilizing a medical device 12 forming cathode 12 using a plurality of the devices 10 of FIG. 1 in accordance with the present invention. The apparatus 30 comprises a plurality of anodes 11 which are substantially equally spaced at predetermined angles θ around a cathode (medical device) 12, and a plurality of ballast resistors 32. Each of the ballast resistors 32 is connected between a separate anode 11 and a common positive voltage source (+V) such as the D.C. voltage source 14 of FIG. 1, while the medical device 12 is coupled to a negative voltage (−V) of the same common voltage source 14. For simplicity, the value of the negative voltage (−V) is assumed to be zero. The potential difference between +V and −V is selected to be sufficient to generate a glow discharge 20 (only shown in FIG. 1) adjacent an outer surface of the medical device 12. With the device 10 of FIG. 1 operating in the Normal or Abnormal Glow Modes, the glow discharge 20 between the anode 11 and cathode 12 only encompasses a portion of the outer surface around the cathode 12. However, when sterilizing a medical device 12, it is desirable to sterilize the entire surface around the medical device 12. To do this, the plurality of anodes 11 are spaced at substantially equal angles θ around the medical device 12 so that the glow discharges 20 (only shown in FIG. 1) produced adjacent the medical device 12 by the anodes 11 overlap each other around the outer surface of the medical device 12. Then, to sterilize a predetermined length of the medical device 12, the medical device 12 is moved along its longitudinal axis 18 while sequential overlapping glow discharges 20 are produced by the anodes 11 both along a first cross-sectional plane of the medical device 12 and along the outer surface parallel to the longitudinal axis 18 of the medical device 12. In this manner, the entire outer surface of a predetermined length of the medical device 12 is sterilized by the overlapping glow discharges 20 as the medical device 12 is moved.

The anodes 11 are driven via independent ballast resistors 32 from a common voltage source 14 (only shown in FIG. 1) in order to prevent a hogging of current by one or more of the anodes 11. In other words, the ballast resistors 32 prevent one or more of the anodes 11 from hogging the current and causing the voltage to drop at the other anodes 11 which would extinguish the glow discharges 20 produced at these other anodes 11. Therefore, the use of the ballast resistors 32 tends to equalize current flow and power dissipation in all of the anodes 11 around the medical device 12. With such current control, every anode 11 is maintained above the breakdown voltage $V_{bV}$, and as one gap 13 breaks down and produces a glow discharge 20, the others will also produce glow discharges 20. With a proper choice of the ballast resistors 32, and the number of anodes 11, the glow discharges 20 formed by the plurality of anodes 11 then merge, and a continuous glow discharge is formed around the outer surface of the medical device 12.

The continuous glow discharges 20 formed by the plurality of anodes 11 and the medical device 12 produce positive and negative ions. The positive ions produced tend to be chemically very reactive and, in particular, impinge on the cathode with excess energy to kill bacteria and other bioburden found on the entire surface around the medical device 12. More particularly, each of the overlapping glow discharges 20 forms species which are neutral, positively charged, and negatively charged, and can also generate heat. For example, each of the overlapping glow discharges 20 generates reactive oxygen ions which oxidize materials on the surface of the medical device 12, and also accelerates reactive oxygen ions and other positively charged species which physically sputter away material found on the surface of the medical device 12. Considerable heat can also be selectively produced by the glow discharge 20 for sterilization purposes if a certain relationship criteria of the current times the voltage less the heat outflow (removal from the area of the glow discharges 20) are met. However, heat is not necessary in accordance with the present invention in order to sterilize the outer surface of the medical device 12, since there are times when it is not desirable to heat the medical device as, for example, when a vaccine or other inoculation fluid is present in a hypodermic needle to be sterilized between egg inoculation procedures, where the heat may destroy the vaccine or other inoculation fluid.

Figure 4:
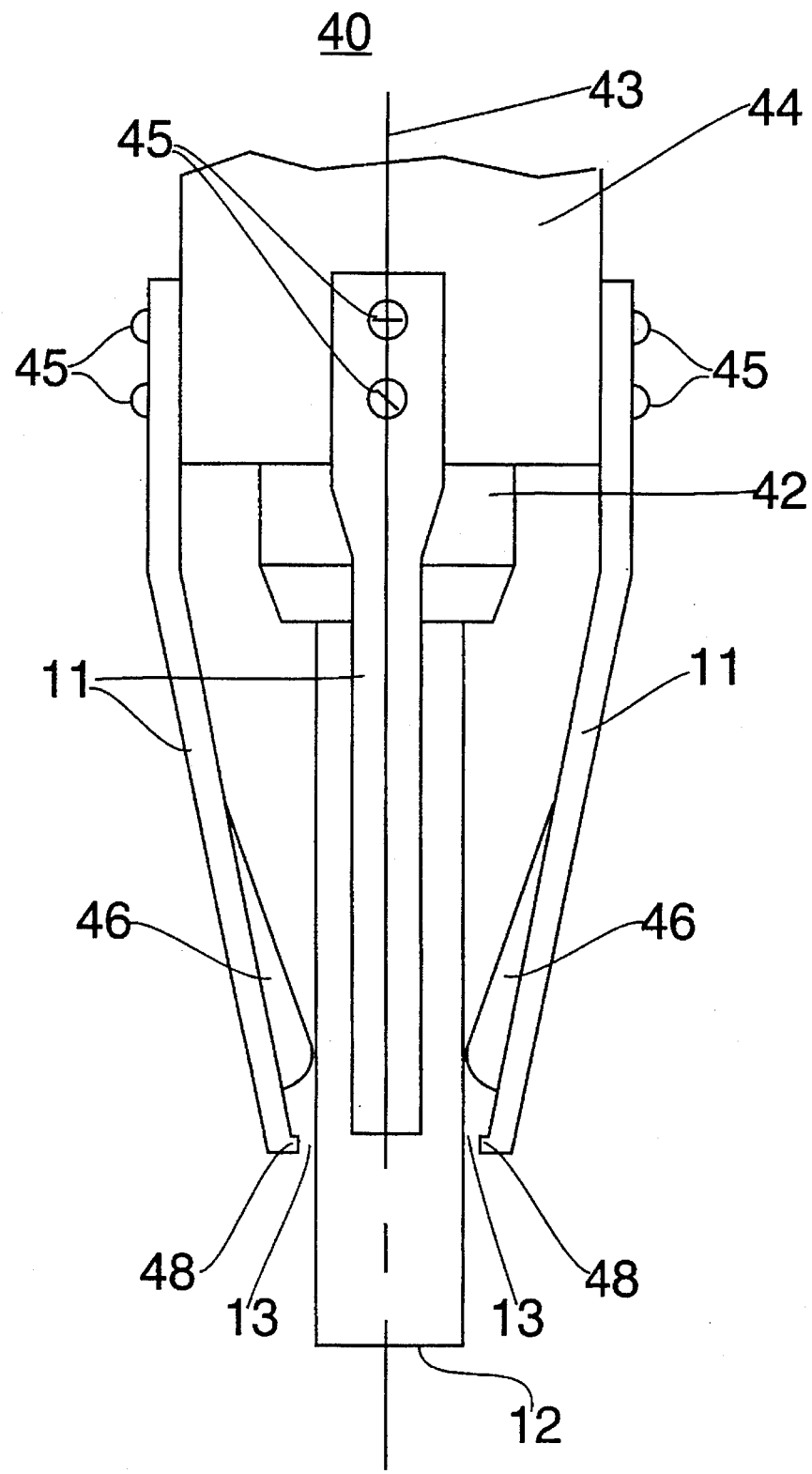
FIG. 4 is side view of a sterilization device in accordance with a first embodiment of the present invention.

Referring now to FIG. 4, there is shown a side view of a sterilization device 40 for use in sterilizing needles in an egg inoculation apparatus in accordance with a first embodiment of the present invention. The sterilization device 40 comprises a first electrically conductive needle 42, a second electrically conductive needle 12, a bushing 44 which performs as a thermal heat sink having an longitudinal aperture (not shown) therethrough wherein the first and second needles 42 and 11 are moveably positioned, and a plurality of electrically conductive flexible projections (electrodes) 11. More particularly, the aperture (not shown) within bushing 44 supports the first needle 42 as the first needle 42 moves along a longitudinal axis 43 of the device 40. The second needle 12 is supported within an aperture (not shown) of the first needle 42 and is independently movable along the longitudinal axis 43 relative to the first needle 42. The second needle has a longitudinal aperture (not shown) therethrough for passing an inoculation fluid into the interior of the egg at predetermined time periods. Each of the first and second needles 42 and 12 are electrically coupled to a negative potential of a voltage source 14 (only shown in FIG. 1) via a switching means 16 (only shown in FIG. 1) to form cathodes when the negative potential is applied thereto.

The flexible projections 11 are each fixedly mounted at one end thereof to the bushing 44 with securing means 45 at substantially equal predetermined angles (e.g., θ as shown in FIG. 3) around the bushing 44, and comprise an anode tip 48 at a second end thereof and a separate electrically insulating spacer 46 formed from, for example, a hard plastic or a ceramic fixedly mounted at a predetermined position therealong. The projections 11 are formed of an electrically conductive material and flex outward when sloped inward edges of the associated spacers 46 contact an outer surface of either one of the first needle 42 or the second needle 12. Each spacer 46 on the associated projection 11 has its maximum inwardly projecting edge area machined to a curved surface that rides on the first needle 42 or the second needle 12 to form a gap 13 with a predetermined length between the inwardly projecting anode tip 48 and the first or second needle 42 or 12 positioned therebeneath. Each of the projections 11 acts as an anode and is coupled to a positive potential of a D.C. voltage source 14 (only shown in FIG. 1) when the switching means 16 (only shown in FIG. 1) is closed.

In operation, the first needle 42 is longitudinally moved downward along the longitudinal axis 43 past the spacers 46 and anode tips 48 of the projections 11 to make a small hole through the shell of an egg (not shown). It is to be understood that as the first needle 42 contacts the spacers 46 in its downward movement, the projections 11 are flexed outwards allowing the first needle 42 to pass thereby and make the small hole in the shell of the egg. The second needle 12 is then moved longitudinally downward through an aperture (not shown) in the first needle 42 and into the interior of the egg to break the membrane therein and inject a chick contained in the egg with a vaccine and/or an inoculation fluid such as one or more growth hormones. The second needle 12 can become contaminated at this point by, for example, a dead chick. Additionally, the tip of the first needle 42 that penetrated the shell can become contaminated from various materials on the shell or from interior fluid from the egg that may touch its tip. Therefore, it is desirable to sterilize each of the first and second needles 42 and 12 prior to their being used to inoculate a second egg in order to avoid contaminating the second egg. The above described general operation of inoculating an egg (without the projections 11) is well-known in the art and is described in, for example, U.S. Pat. No. 5,158,038 (O. Sheeks et al.), issued on Oct. 27, 1992, and U.S. Pat. No. 4,040,388 (G. Miller), issued on Aug. 9, 1977.

In accordance with the first embodiment of the present invention, the first and second needle 42 and 12 are individually sterilized by, for example, first retracting the first needle 42 upwards towards the bushing 44. As a predetermined portion of the first needle 42, including its end that penetrated the egg shell, is moved past the anode tips 48 of the plurality of the projections 11, the positive and negative voltages are applied to the projections 11 and the first needle 42, respectively, to form a sequence of overlapping glow discharges 20 (only shown in FIG. 1) adjacent the first needle 42. More particularly, the spacer 46 of each projection 11 is in contact with the outer surface of the first needle 42 to form a gap 13 having a predetermined length (e.g., 0.0005" to 0.006") between the anode tip 48 and the first needle 42. The gap 13 is dependent on the difference between maximum inward projection of the anode tip 48 and the maximum inward projection of the spacer 46. Therefore, the gap is preferably controlled by a machining of the spacer 46 using any suitable tool (not shown). The potential at each of the gaps 13 is raised to the breakdown voltage ($V_{bv}$) as shown in FIG. 2, and then to the sustaining voltage ($V_{sust}$) to produce the glow discharge 20 adjacent the first needle 42. This produces a continuous glow discharge around one cross-sectional area of the first needle 42. Then, as the first needle 42 is moved longitudinally towards the bushing 44, subsequent cyclical overlapping glow discharges 20 are formed in the same manner along the predetermined length to be sterilized, by, for example, cyclically opening and closing the switching means 16 (only shown in FIG. 1) with a proper timing. As stated hereinbefore, the continuous glow discharges 20 formed by the plurality of projections 11 and the first needle 42 produce positive and negative ions that tend to chemically react and sputter to kill bacteria on the entire surface around the first needle 42. Each of the overlapping glow discharges 20 both around and along the first needle 42 form species which are neutral, positively charged, and negatively charged, and can also generate heat. In this manner, the desired portion of the first needle 42 is sterilized. Once the predetermined portion of the first needle 42 is sterilized by the glow discharges 20, the first needle 42 is further retracted a sufficient distance towards the bushing 44 so that the spacers 46 on the projections 11 now contact the outer surface of the second needle 12.

With the first needle 42 sterilized and moved out of the way, the second needle 12 is retracted upwards from within the egg (not shown) towards the bushing 44. Since the first needle 42 was retracted beyond the spacers 46, the gaps 13 between the ends of the projections 11 and the second needle 12 are substantially the same dimensions (or width range) as were found with the first needle 42. Therefore, as a predetermined portion of the second needle 12, including at least the portion that entered the egg, is moved past the anode tips 48 of the projections 11, a sequence of overlapping glow discharges 20 (only shown in FIG. 1) both around and along the second needle 12 are formed to sterilize the second needle 12. It is to be understood that the sustaining voltage ($V_{sust}$) and the current used to form the glow discharges 20 for sterilizing the second needle 12 preferably provides little or no heat, or at maximum a temperature rise which is insufficient to destroy or damage the bulk of the vaccine or inoculation fluid presently stored in the second needle 12.

Figure 5:
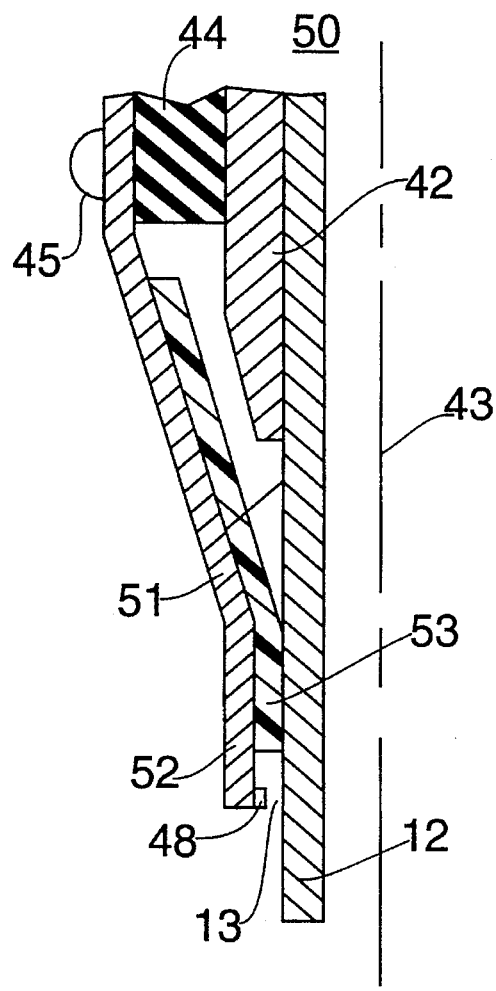
FIG. 5 is a cross-sectional view of a modified portion of the sterilization device of FIG. 4 in the area of an anode projection.

Referring now to FIG. 5, there is shown a cross-sectional view of a portion 50 corresponding to the area of the projections 11 of the sterilization device 40 of FIG. 4. The portion 50 shows a first needle 42, a second needle 12, a bushing 44 which serves as a heat sink in which the first and second needles are supported for movement parallel to a longitudinal axis 43, and a projection (electrode) 51 which replaces each of the projections (electrode) 11 in the sterilization device 40 of FIG. 4. More particularly, a first end section of the projection 51 is secured with securing means 45 to the bushing 44 and is angled inward from the bushing 44 for a predetermined distance to a second end section 52 which is oriented substantially parallel to an outer surface of the first needle 42 and the second needle 12. The projection 51 comprises an anode tip 48 projecting inwardly a desired distance (e.g., 0.008") at the end of the second end section 52, and a spacer 53 formed from, for example, a self-adhesive electrically insulating transfer tape which is fixedly mounted onto an inner surface of each projection 51 along a part of the second end section 52. The spacer 53 replaces the spacer 46 shown in the sterilization device 40 of FIG. 4, and is machined or ground in situ to a predetermined thickness along the second end section 52 to provide a gap 13 with a predetermined length between the anode tip 48 and either one of the first needle 41 or the second needle 12 when positioned therebeneath. The self-adhesive plastic transfer tape used for the spacer 53 is preferably a high voltage dielectric transfer tape which is commercially available and is obtainable with accurate thicknesses (e.g., 0.012 inches). Once fixedly mounted on the inner surface of the projection 51, the thickness of the transfer tape forming the spacer 53 can then be ground down along the second end section 52 to a desired thickness (e.g., 0.010") with a tool (not shown) containing a raised abrasive region. The manufacturing these anode electrode without requiring the fancy machining required for the spacers 46 of the sterilization device 40 of FIG. 4. When the transfer tape of spacer 53 wears down with extended use, it is easily replaced with a new section of transfer tape and machined to a proper dimension.

Figure 6:
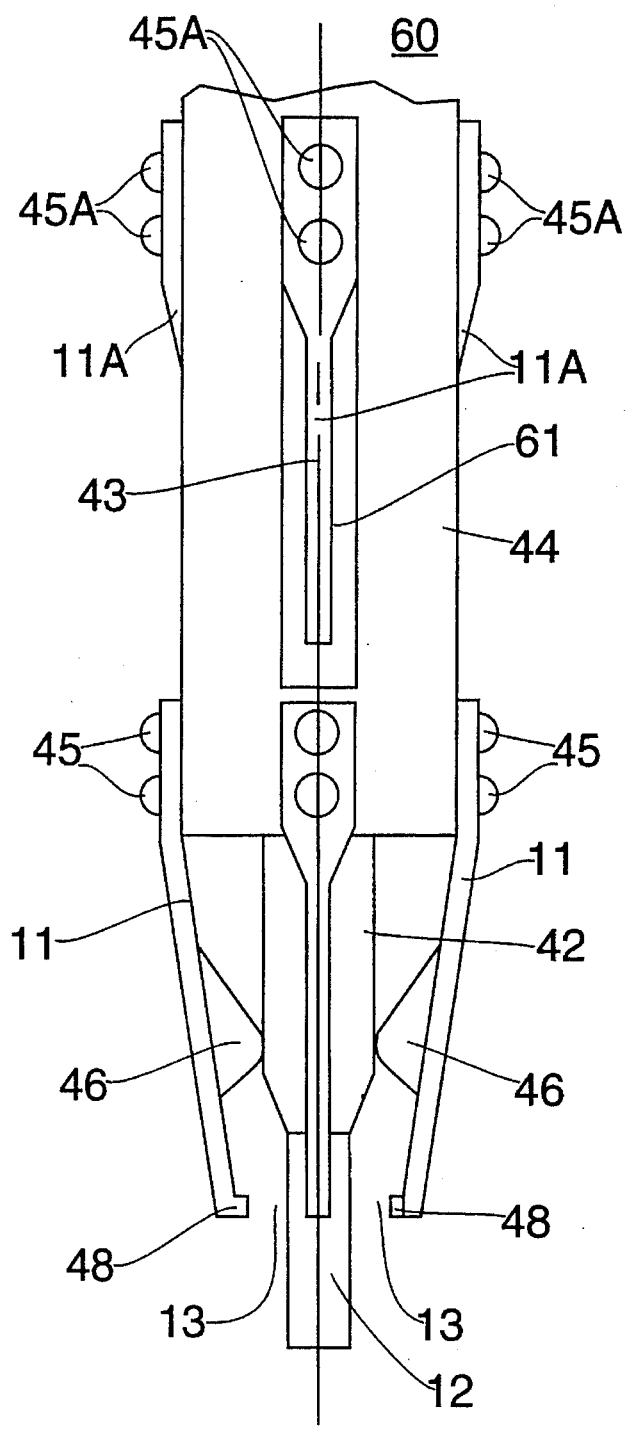
FIG. 6 is a side view of a sterilization device in accordance with a second embodiment of the present invention.

Referring now to FIG. 6, there is shown a side view of a sterilization device 60 for sterilizing needles in an egg inoculation apparatus in accordance with a second embodiment of the present invention. The sterilization device 60 is an extension of the sterilization device 40 of FIG. 4 and comprises a first electrically conductive needle 42, a second electrically conductive needle 12, a bushing 44 which acts as a heat sink having a longitudinal aperture (not shown) therethrough wherein the first and second needles 42 and 11 are moveably positioned, a plurality of first electrically conductive flexible projections (electrodes) 11, and a plurality of second electrically conductive flexible projections (electrodes) 11A. The plurality of first electrically conductive flexible projections 11 are fixedly mounted to a side surface and at one end of the bushing 44 with securing means 45 at substantially equal predetermined angles (e.g., $\theta$ as shown in FIG. 3) around the bushing 44. Each first projection 11 comprises an anode tip 48 at a second end thereof and a separate electrically insulating spacer 46 fixedly mounted at a predetermined position therealong and formed from, for example, a hard plastic. The first projections 11 are formed from an electrically conductive material that flex outward when sloped inward edges of the associated spacers 46 contact the outer surface of either one of the first needle 42 or the second needle 12. Each spacer 46 on the associated first projection 11 has its maximum inwardly projecting edge area machined to a curved surface that rides on the first needle 42 or the second needle 12 to form a gap 13 with a predetermined length between the inwardly projecting anode tip 48 and the first or second needle 42 or 12 positioned therebeneath. Each of the first projections 11 is coupled to a positive potential of a D.C. voltage source 14 (only shown in FIG. 1) when the switching means 16 (only shown in FIG. 1) is closed to form an anode.

The plurality of second electrically conductive flexible projections 11A are fixedly mounted to a side surface of the bushing 44 with securing means 45A above the plurality of first projections 11 and at substantially equal predetermined angles (e.g., $\theta$ as shown in FIG. 3) around the bushing 44. Each second projection 11A angles inwards through a rectangular aperture 61 in the bushing 44, and has a configuration corresponding to that of the first projection 11. More particularly, each second projection 11A comprises an anode tip 48A (not shown) at a second end thereof and a separate spacer 46A (not shown) formed from, for example, a hard plastic fixedly mounted at a predetermined position therealong. The second projections 11A are formed of an electrically conductive material and flex outward when sloped inward edges of the associated spacers 46A contact the outer surface of either one of the first needle 42 or the second needle 12. Each spacer 46A on the associated second projection 11A has its maximum inwardly projecting edge area machined to a curved surface that rides on the first needle 42 and the second needle 12 to form a gap 13A (not shown) with a predetermined length between the inwardly projecting anode tip 48A and the first or second needle 42 or 12 positioned therebeneath. Each of the second projections 11A is coupled to a positive potential of a D.C. voltage source 14 (only shown in FIG. 1) when the switching means 16 (only shown in FIG. 1) is closed to form an anode. It is to be understood that the bushing 44 can be extended to enclose the plurality of first projections 11 similar to that provided for the plurality of second projections 11A.

In operation, the first needle 42 is longitudinally moved downward along a longitudinal axis 43 past the spacers 46 and anode tips 48 of the first and second projections 11 and 11A to make a small hole through the shell of an egg (not shown). It is to be understood that as the first needle 42 contacts the spacers 46A of the second projections 11A and then the spacers 46 of the first projections 11 in its downward movement so that the second and first projections 11A and 11 are flexed outwards allowing the first needle 42 to pass thereby and make the small hole in the shell of the egg. The second needle 12 is then moved longitudinally downward through an aperture (not shown) in the first needle 42 and into the interior of the egg to break the membrane therein and inject a chick contained therein with a vaccine and/or other inoculation fluid such as one or more growth hormones. The second needle 12 can become contaminated at this point by, for example, a dead chick. Additionally, the tip of the first needle 42 that penetrated the shell can become contaminated from various materials on the shell or from interior fluid that may touch its tip. Therefore, it is desirable to sterilize each of the first and second needles 42 and 12 prior to their being used to inoculate a second egg in order to avoid contaminating the second egg.

The first and second needles 42 and 12 of device 60 of FIG. 6 are individually sterilized by, for example, first retracting the first needle 42 upwards towards the bushing 44. As a predetermined portion of the first needle 42, including its end that penetrated the egg shell, is moved past the anode tips 48A (not shown) of the plurality of the second projections 11A, positive and negative voltages are applied to the second projections 11A and the first needle 42, respectively, to form a sequence of overlapping glow discharges 20 (only shown in FIG. 1) adjacent the outer surface of the first needle 42. More particularly, the spacer 46A (not shown) of each second projection 11A is in contact with the outer surface of the first needle 42 to form a gap 13A (not shown) having a predetermined length (e.g., 0.0005" to 0.0025") between the anode tip 48A and the first needle 42. The gap 13A is dependent on the difference between maximum inward projection of the anode tip 48A and the maximum inward projection of the spacer 46A. Therefore, the gap 13A is preferably controlled by a machining of the spacer 46A using a suitable tool. The potential at each of the gaps 13A is brought up to the breakdown voltage ($V_{bv}$) as shown in FIG. 2, and then to the sustaining voltage ($V_{sust}$) to produce the glow discharge 20 adjacent the first needle 42. This produces a continuous glow discharge around one cross-section of the first needle 42. Then, as the first needle 42 is moved longitudinally into the bushing 44, subsequent cyclical overlapping glow discharges 20 are formed in the same manner along the predetermined length to be sterilized, by, for example, cyclically opening and closing the switching means 16 (shown only in FIG. 1) with a desired proper timing.

The second needle 12 is then retracted upwards towards the bushing 44. As a predetermined portion of the second needle 12, including its end that penetrated the egg shell, is moved past the anode tips 48 of the plurality of the first projections 11, the positive and negative voltages are applied to the first projections 11 and the second needle 12, respectively, to form a sequence of overlapping glow discharges 20 (only shown in FIG. 1) adjacent outer surface of the second needle 12. More particularly, the spacer 46 of each first projection 11 is in contact (not shown) with the outer surface of the second needle 12 to form a gap 13 having a predetermined length (e.g., 0.0005" to 0.006") between the anode tip 48 and the second needle 12. The gap 13 is dependent on the difference between maximum inward projection of the anode tip 48 and the maximum inward projection of the spacer 46. Therefore, the gap 13 is preferably controlled by a machining of the spacer 46 using any suitable tool.

As stated hereinbefore, the continuous glow discharges 20 formed by the plurality of second projections 11A and the first needle 42 and the first projections 11 and the second needle 12 produce positive and negative ions that tend to chemically react and sputter to kill bacteria on the entire surface around the first needle 42 and the second needle 12. Each of the overlapping glow discharges 20 both around and along the outer surface of the first needle 42 and the second needle 12 form species which are neutral, positively charged, and negatively charged, and can also generate heat. In this manner, the desired portions of the first needle 42 and the second needle 12 are sterilized. It is to be understood that the sterilization of the first needle 42 and the second needle 12 can be performed concurrently or serially.

In order to make sure that the sterilization has actually taken place in each of the sterilization devices 40 and 60 of FIGS. 4 and 6, respectively, a current sensing means 19 (only shown in FIG. 1) is provided for monitoring the current in each wire from the voltage source 14 (only shown in FIG. 1) to each of the first and second projections 11 and 11A. If a correct current value is achieved in each of the wires from the voltage source 14 to the first and second projections 11 and 11A when the glow discharges 20 are activated, then a positive identification is provided that each glow discharge 20 is on and is sterilizing the outer surface of the associated first 42 and second 12 needles. Knowing what the total voltage used was, and determining the temperature achieved at each first and second needle 42 and 12 from the current and voltage values applied to each second and first projection 11A and 11, respectively, a technique is provided for verifying that the first and second needles 42 and 12 have been sterilized. In other words, devices as, for example, ammeters, voltmeters, etc. are connected to the D.C. voltage source 14 (only shown in FIG. 1) to provide indications of whatever information is required to confirm that the proper sterilization was performed.

The sterilization devices 40 and 60 of FIGS. 4 and 6, respectively, provide arrangements for sterilizing medical devices 12 that are formed with electrically conductive materials and have a substantially regular shape in a few seconds. A substantially regular shape is defined for purposes of the present invention as a device that has no irregular steps or corners, but may have a sharp edge ( e.g. a surgical knife), along a section to be sterilized where it is difficult to maintain a gap 13 with a predetermined length therealong. It is to be understood that a medical device having irregular steps can be redesigned to have a substantially regular shape in the area to be sterilized. It is to be further understood that nothing that adheres to an outer surface of a medical device, such as bacteria, etc., is able to withstand being destroyed by the glow discharges 20.

Figure 7:
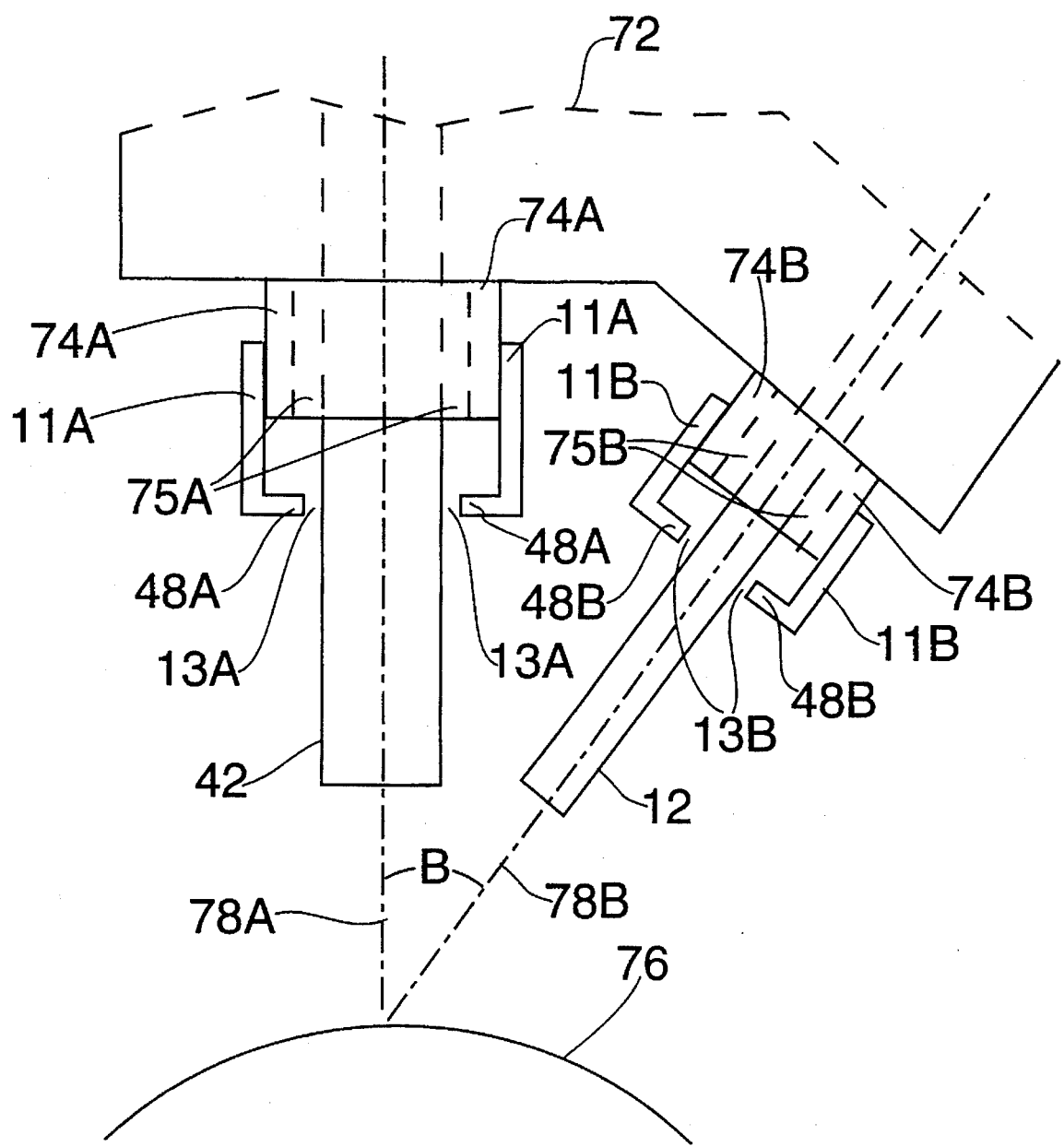
FIG. 7 is side view of a sterilization device in accordance with a third embodiment of the present invention.

Referring now to FIG. 7, there is shown a side view of a sterilization device 70 for use in sterilizing needles in an egg inoculation apparatus in accordance with a third and presently preferred embodiment of the present invention. The sterilization device 70 comprises a plate 72, a first bushing 75A, a first insulating spacer 74A, a first electrically conductive needle 42, a plurality of first electrically conductive anode projections 11A (electrodes, of which only two anode projections 11A are shown) where each anode projection 11A comprises a separate anode tip 48A, a second bushing 75B, a second insulating spacer 74B, a second electrically conductive needle 12, a plurality of second electrically conductive anode projections 11B (electrodes, of which only two anode projections 11B are shown) where each anode projection 11B comprises a separate anode tip 48B. More particularly, the plate 72 supports the first and second bushings 75A and 75B in a predetermined fixed relationship to each other, and the combination of the plate 72 and the first and second bushings 75A and 75B act as heat sinks for the sterilization device 70. Still further, the plate 72 and the first bushing 75A define a longitudinal aperture therethrough wherein the first needle 42 is moveably supported. The first needle 42 is shown completely occupying the longitudinal aperture. The plate 72 and the second bushing 75B also define a longitudinal aperture therethrough wherein the second needle 12 is moveably supported. The second needle 12 is shown completely occupying the longitudinal aperture.

The sterilization device 70 is shown located in proximity to an egg 76 (of which only the top surface is shown) to be inoculated which is temporarily fixedly supported by any suitable supporting means (not shown). The longitudinal aperture defined within the first bushing 75A supports the first needle 42 as the first needle 42 is moved along a first longitudinal axis 78A which is substantially perpendicular to a surface (shell) of the egg 76. The second needle 12 is moveably supported within the longitudinal aperture defined in the second bushing 75B as the second needle 12 is moved along a second longitudinal axis 78B. The second longitudinal axis 78B is arranged at a predetermined angle β to the first longitudinal axis 78A and substantially intersects the first longitudinal axis 78A at the surface of the egg 76. The second needle 12 defines a longitudinal aperture (not shown) therethrough for passing an inoculation fluid into the interior of the egg 76 at predetermined time periods. Each of the first and second needles 42 and 12 are electrically coupled to a negative or ground potential of a voltage source 14 (shown only in FIG. 1) to form cathodes when the negative or ground potential is applied.

First ends of the first and second flexible anode projections 11A and 11B are fixedly mounted at substantially equal angles (as shown in FIGS. 4 and 6) around each of the first and second bushings 75A and 75B, respectively, and are insulated from the respective first and second bushings 75A and 75B by the first and second insulating spacers 74A and 74B, respectively. It should be understood that although only two of each of the plurality of first and second anode projections 11A and 11B are shown, other first and second anode projections 11A and 11B are provided at predetermined substantially equal angles around the bushings 75A and 75B, respectively. The anode projections 11A and 11B each comprise a series of anode tips 48A and 48B, respectively, at a second end thereof. The anode projections 11A and 11B are formed of an electrically conductive material, and are coupled to a positive potential of the voltage source 14 (shown only in FIG. 1) to form anodes when the positive potential is applied.

In operation, the first needle 42 is longitudinally moved downward along the longitudinal axis 78A past the anode tips 48A of the first anode projections 11A to make a small hole (not shown) through the shell of the egg 76. The first needle 42 is then retracted towards the first bushing 75A along the first longitudinal axis 78A. As the first needle 42 is retracted, predetermined positive and negative (or ground) potentials are applied to the anode projections 11A and first needle 42, respectively, to form glow discharges (shown only in FIG. 1) which encircle and sterilize the first needle 42. The first needle 42 is preferably retracted to a point where the glow discharges are around an end of the first needle 42. Concurrent with the first needle 42 being retracted, the second needle 12 is moved downward along the second longitudinal axis 78B to pass through the hole in the shell of the egg 76 and into the egg membrane (not shown) to inoculate the egg 76. The second needle 12 is then withdrawn from the egg 76 and retracted upward along the second longitudinal axis 78B towards second bushing 75B. As the second needle 12 is withdrawn from the egg 76 and further retracted, predetermined positive and negative (or ground) potentials are applied to the anode projections 11B and second needle 12, respectively, to form glow discharges (shown only in FIG. 1) which encircle and sterilize the second needle 12. Sterilization of the first and second needles 42 and 12 by the separate glow discharges formed adjacent the first and second needles 42 and 12 an near the anode tips 48A and 48B, respectively, of the anode projections 11A and 11b is performed along at least the length of the first and second needles 42 and 12 that had any contact with the egg 76 as the first and second needles 42 and 12 are retracted.

When the first needle 42 or second needle 12 is being retracted upwards at, for example, 1 cm/sec (which is a fairly slow velocity), a temperature rise in the needle 42 or 12 adjacent the glow discharges is in the order of, for example, about 30 degrees Centigrade. If the needle 42 or 12 is retracted at, for example, 10 cm/sec, a temperature rise in the needle 42 or 12 adjacent the glow discharges is in the order of, for example, a couple of degrees Centigrade. Therefore, as the needles 42 and 12 are being retracted, the temperature of the needles 42 and 12 produced by the glow discharges is quite low without doing anything to control the average voltage being applied to the anode projections 11A and 11B and the first and second needles 42 and 12, respectively. It is to be understood that while the first and second needles 42 and 12 are being separately sterilized along a length thereof during the retracting phase, the retraction of each of the first and second needles 42 and 12 can be stopped at a point where the glow discharges are continuously maintained adjacent the ends of the first and second needles 42 and 12. With the glow discharges being continuously maintained, the temperature in the area of the ends of the first and second needles 42 and 12 will rise and can reach a temperature of, for example, 700 degrees Centigrade.

Raising the temperature of the ends of one or both of the first and second needles 42 and 12 can produce certain advantages. For example, if the temperature of the end of the first needle 42 is raised to a predetermined temperature, the heated end of the first needle 42 can be moved downward into the hole after the egg 76 has been inoculated by the second needle 12 to coagulate egg albumin and seal the egg 76. Alternatively, a third needle (not shown) which is disposed along a longitudinal axis (not shown) which is at an angle β from the longitudinal axis 78A but located on a side opposite the longitudinal axis 78B can be used to coagulate the egg material. However, if the first needle 42 is used to coagulate the egg material, then it is again sterilized by the glow discharges as the first needle is retracted because it contacted the egg 76. Since the first bushing 75A and the plate 72 act as a heat sink, the encircling glow discharges only raise the temperature of a very small length of about one or two millimeters adjacent the end of the first needle 42.

If the temperature of an end section of the second needle 12 is raised to a predetermined temperature of for example 700 degrees Centigrade by maintaining continuous glow discharges around the end section for a predetermined time period, the end section of the second needle 12 is further sterilized by the high temperature. This is equivalent to placing the end section of the second needle in a flame to sterilize it. More particularly, since the second bushing 75B and the plate 72 act as a heat sink, the glow discharges encircling the end area of the second needle 12 only raise the temperature of the second needle 12 for a length of about one or two millimeters adjacent the end of the second needle 12. By locally heating the end section of the second needle 12, it vaporizes any bacteria, etc. that is located within the one or two millimeters on the inner and outer surfaces of the second needle 12 adjacent the end of the second needle 12. Concurrently, the higher temperature also evaporates about one-tenth microliter of any vaccine located in the longitudinal aperture defined by the second needle 12 adjacent the end of the second needle 12. Therefore, the sterilization process can apply cool glow discharges along a length of the first and second needles 42 and 12 which provides predetermined sterilization (cleaning) properties in the areas touched by the glow discharges, and localized heat by continuously maintaining glow discharges at a predetermined area around the first or second needles 42 and 12. The combination of the cool glow discharge sterilization and localized heat sterilization provides a maximum efficiency in killing or vaporizing bacteria or other bioburden on the first and second needles 42 and 12 or other medical devices. Once a proper high temperature is reached, the glow discharges are extinguished and the second needle is allowed to cool before a next injection into a second egg 76. Such cooling generally is accomplished in a range of from a fraction of a second to a few seconds due to time constants which are involved. It is to be understood that the plate 72 can define separate bores (not shown) which encircle, but do not touch, each of the bushings 75A and 75B and the associated anode projections 11A and 11B, respectively, associated with the first and second needles 42 and 12.

Figure 8:
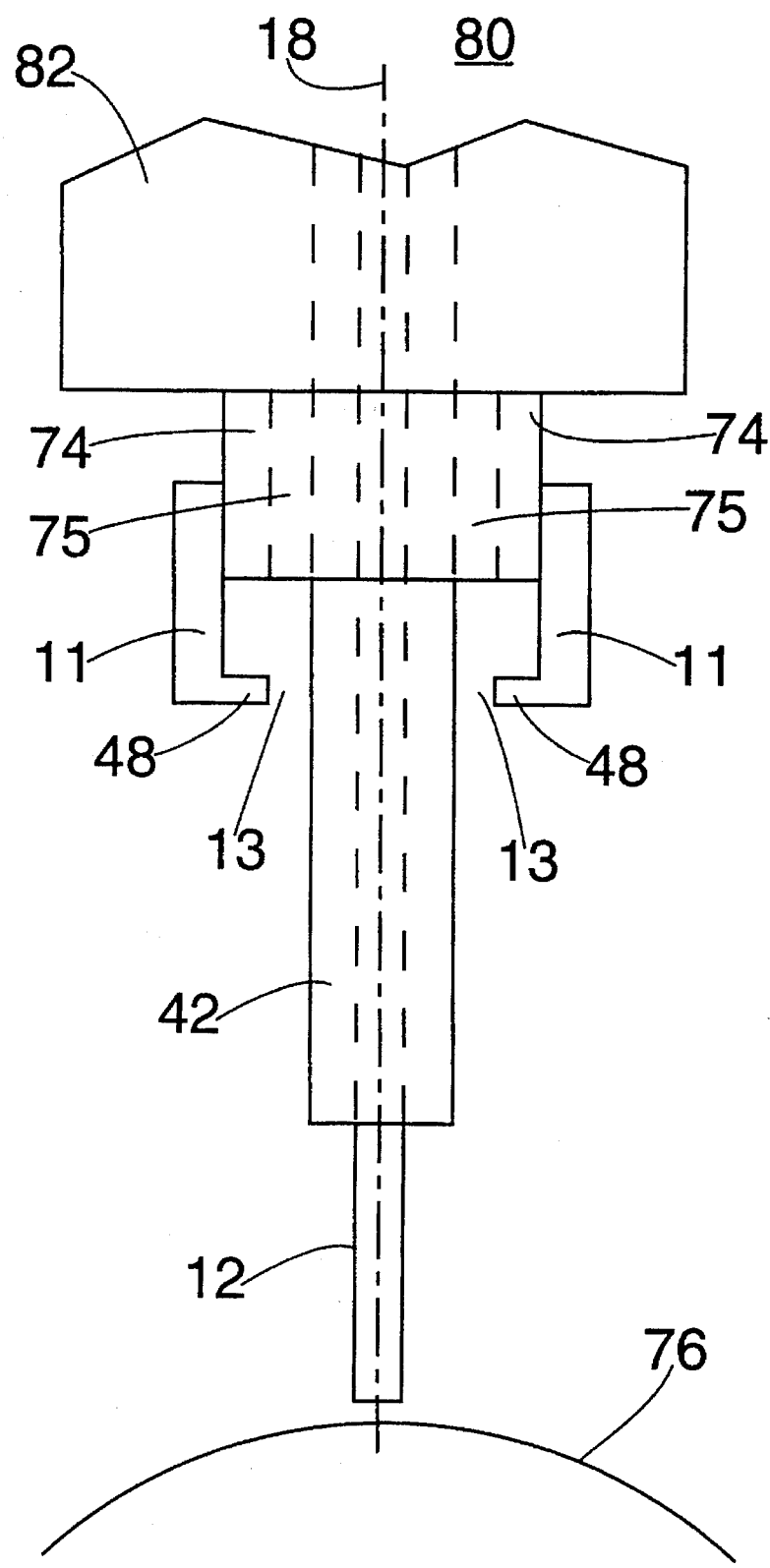
FIG. 8 is a side view of a sterilization device in accordance with a fourth embodiment of the present invention.

Referring now to FIG. 8, there is shown a side view of a sterilization device 80 for use in sterilizing injection needles in an egg inoculation apparatus in accordance with a fourth embodiment of the present invention. The sterilization device 80 comprises a plate 82, a bushing 75, an insulating spacer 74 surrounding the bushing 75, a first electrically conductive needle 42, a plurality of first electrically conductive rigid anode projections 11 (electrodes, of which only two anode projections 11 are shown) where each anode projection 11 comprises an anode tip 48, and a second electrically conductive needle 12. More particularly, the plate 82 fixedly supports the bushing 75, and the combination of the plate 82 and the bushing 75 act as a heat sink for the sterilization device 80. Still further, the plate 82 and the bushing 75 define a longitudinal aperture therethrough wherein the first needle 42 is moveably supported. The first needle 42 is shown completely occupying the longitudinal aperture defined by the bushing 75. The first needle 42 defines a longitudinal aperture therethrough wherein the second needle 12 is moveably supported. The second needle 12 is shown completely occupying the longitudinal aperture of the first needle 42.

The sterilization device 80 is located in proximity to an egg 76 (of which only the top surface is shown) to be inoculated which is temporarily fixedly supported by any suitable supporting means (not shown). The longitudinal aperture defined within the bushing 75 supports the first needle 42 as the first needle 42 is moved along a longitudinal axis 18 which is substantially perpendicular to a surface (shell) of the egg 76. The second needle 12 is moveably supported within the longitudinal aperture defined in the first needle 42 as the second needle 12 is moved along the longitudinal axis 18. The second needle 12 defines a longitudinal aperture (not shown) therethrough for passing an inoculation fluid into the interior of the egg 76 at predetermined time periods. Each of the first and second needles 42 and 12 are electrically coupled to a negative or ground potential of a voltage source 14 (shown only in FIG. 1) to form cathodes when the negative or ground potential is applied.

First ends of the rigid anode projections 11 are fixedly mounted at substantially equal angles (as shown in FIGS. 4 and 6) around the bushing 75, and are insulated from the bushing 75 by the insulating spacer 74. It should be understood that although only two of the plurality of rigid anode projections 11 are shown, other rigid anode projections 11 are provided at predetermined substantially equal angles around the bushing 75. Each of the anode projections 11 comprises an anode tip 48 at a second end thereof. The rigid anode projections 11 are formed of an electrically conductive material, and are coupled to a positive potential of the voltage source 14 (shown only in FIG. 1) to form anodes when the positive potential is applied.

To inoculate the egg 76, the first needle 42 is longitudinally moved downward along the longitudinal axis 18 past the anode tips 48 of the anode projections 11 to make a small hole (not shown) through the shell of the egg 76. The first needle 42 is then retracted towards the bushing 75 along the longitudinal axis 18. As the first needle 42 is retracted, predetermined positive and negative (or ground) potentials are applied to the anode projections 11 and first needle 42, respectively, to form glow discharges (shown only in FIG. 1) which encircle and sterilize the first needle 42. After the first needle 42 has made a hole in the egg 76 and starts to retract, the second needle 12 is moved downward along the longitudinal axis 18 to pass through the hole in the shell of the egg 76 and into the egg membrane (not shown) to inoculate the egg 76. The second needle 12 is then withdrawn from the egg 76 and retracted upward along the longitudinal axis 18 with the first needle 42 towards bushing 75. As the second needle 12 is withdrawn from the egg 76 and further retracted at the same speed as the first needle 42, which is being sterilized by the glow discharges, a negative (or ground) potential is also applied to the second needle 12 to form glow discharges (shown only in FIG. 1) around the second needle 12 when the second needle 12 is aligned near the anode projections 11. These glow discharges encircle and sterilize the second needle 12 when the second needle 12 moves near the tips 48 of the anode projections 11 after the end of the first needle 42 passes thereby. Sterilization of the first and second needles 42 and 12 by the glow discharges is performed along at least the length of the first and second needles 42 and 12 that had any contact with the egg 76 as the first and second needles 42 and 12 are retracted.

In sterilization device 80, the glow discharges (shown only in FIG. 1) first move down the first needle 42 as the first needle 42 is retracted towards the bushing 75. The glow discharges are then transferred without interruption from the end of the first needle 42 to the shaft of the second needle 12 where the second needle 12 projects from the end of the first needle 42 as both needles are concurrently retracted. The sterilization device 80 illustrates that the glow discharges, once initiated, are capable of being transferred along a medical device that has shapes of different widths within predetermined limits as the medical device is moved past the anode projections 11. Therefore, the sterilization device 80 is capable of sterilizing any medical device which has a somewhat irregular shape such as dental burr which include circles of revolution and different diameters as the length of a dental burr is traversed.

In sterilization device 80, the length of a gap 13 between the tip 48 of each rigid anode projection 11 and the outer surface of the second needle 42 is different than the length of the gap 13 between the tip 48 of each rigid anode projection 11 and the outer surface of the second needle 12. In order for the glow discharges to transfer to different portions of a medical device having different diameters or widths, such glow discharge transfer occurs if a critical point is not reached. More particularly, once a glow discharge is initiated, the glow discharge continues until a critical point is reached where the losses due to ions of the glow discharge reach a point where the losses cannot be sustained by the current that is flowing between the anode projections 11 and cathode (needle 42 or 12). This illustrates that a different physical condition in the sterilization device 80 is responsible for each of the initiation and the termination of a glow discharge. For example, a glow discharge can be initiated with a gap 13 of a couple of microns or tenths of a mil between the tips 48 of the anode projections 11 and the first needle 42 and the gap widened to as much as 50 mils before a critical point is reached where the glow discharge terminates. Therefore, once initiated, the glow discharge continues down the outer surface of the first needle 42 unless the critical point is reached where the losses cannot sustain the glow discharge. The glow discharge then transfers to the outer surface of the second needle 12 unless the critical point is reached where the losses cannot sustain the glow discharge. Therefore, with sterilization device 80, it is preferable that the sterilization process be started at a point where an irregular shaped medical device has its widest cross-section to have a minimal gap 13 that supports a glow discharge. The sterilization device 80 is similar to the sterilization device 40 of FIG. 4 except that the anode projections 11 of the sterilization device 80 do not flex. Therefore, the tips 48 of the anode projections 11 of the sterilization device 80 provide different length gaps with a medical device having different cross-sectional dimensions along its length as the medical device traverses past the tips 48.

Figure 9:
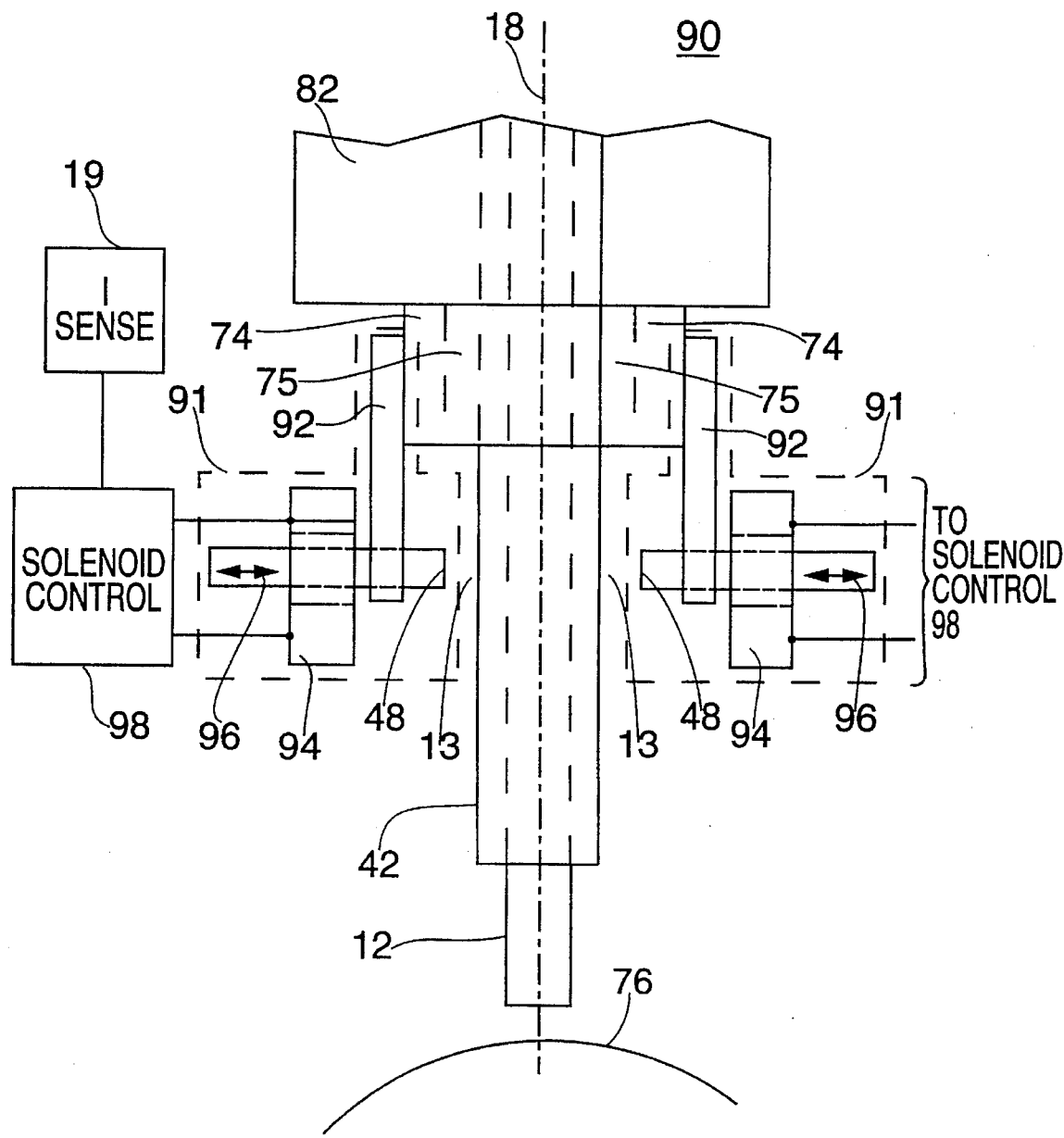
FIG. 9 is a side view of a sterilization device in accordance with a fifth embodiment of the present invention, The drawings are not necessarily to scale.

Referring now to FIG. 9, there is shown a side view of a sterilizing device 90 for use in sterilizing injection needles in an egg inoculation apparatus in accordance with a fifth embodiment of the present invention. The sterilization device 90 comprises a plate 82, a bushing 75, an insulating spacer 74 surrounding the bushing 75, a first electrically conductive needle 42, a plurality of electrically conductive anode assemblies 91 (shown within a dashed line rectangle), and a second electrically conductive needle 12. The anode assemblies 91 form electrodes of which only two anode projections 91 are shown. Each anode assembly 91 is shown as a solenoid comprising a coil 94 that is coupled to a solenoid control 98, and an armature comprising a flexible mounting device 92 and a magnetic rod 96 having an anode tip 48. More particularly, the plate 82 fixedly supports the bushing 75, and the combination of the plate 82 and the bushing 75 act as a heat sink for the sterilization device 90. Still further, the plate 82 and the bushing 75 define a longitudinal aperture therethrough wherein the first needle 42 is moveably supported. The first needle 42 is shown completely occupying the longitudinal aperture defined by the bushing 75. The first needle 42 also defines a longitudinal aperture therethrough wherein the second needle 12 is moveably supported. The second needle 12 is shown completely occupying the longitudinal aperture defined by the first needle 42.

First ends of the anode assemblies 91 are fixedly mounted at substantially equal angles (as shown in FIGS. 4 and 6) around the bushing 75, and are insulated from the bushing 75 by the insulating spacer 74. It should be understood that although only two of the plurality of anode assemblies 91 are shown, other anode assemblies 91 are provided at predetermined substantially equal angles around the bushing 75. The magnetic armatures 96 of the anode assemblies 91 are formed of an electrically conductive material, and are coupled to a positive potential of the voltage source 14 (shown only in FIG. 1) to form anodes when the positive potential is applied.

The sterilization device 90 is shown located in proximity to an egg 76 (of which only the top surface is shown) to be inoculated. The longitudinal aperture defined within the bushing 75 supports the first needle 42 as the first needle 42 is moved along a longitudinal axis 18 which is substantially perpendicular to a surface (shell) of the egg 76. The second needle 12 is moveably supported within the longitudinal aperture defined in the first needle 42 as the second needle 12 is moved along the longitudinal axis 18. The second needle 12 defines a longitudinal aperture (not shown) therethrough for passing an inoculation fluid into the interior of the egg 76 at predetermined time periods. Each of the first and second needles 42 and 12 are electrically coupled to a negative or ground potential of a voltage source 14 (shown only in FIG. 1) to form cathodes when the negative or ground potential is applied.

To inoculate the egg 76, the first needle 42 is longitudinally moved downward along the longitudinal axis 18 past the anode tips 48 of the anode assemblies 91 to make a small hole (not shown) through the shell of the egg 76. The first needle 42 is then retracted a predetermined distance towards the bushing 75 along the longitudinal axis 18. The second needle 12 is then moved downward along the longitudinal axis 18 to pass through the hole in the shell of the egg 76 and into the egg membrane (not shown) to inoculate the egg 76. The second needle 12 is then withdrawn from the egg 76 and is retracted upward along the longitudinal axis 18 with the first needle 42 towards bushing 75 at a predetermined speed. At this time the sterilization process of the first and second needles 42 and 12 is started using glow discharges. Sterilization of the first and second needles 42 and 12 by the glow discharges is performed along at least the length of the first and second needles 42 and 12 that had any contact with the egg 76 as the first and second needles 42 and 12 are retracted.

In operation, prior to starting a sterilization of the first and second needles 42 and 12 or any other medical device, a length of a gap 13 between each tip 48 of the anode assemblies 91 and the outer surface of the first needle 42 (having the larger diameter) is longer than a gap 13 with which a glow discharge can be initiated. When the sterilization of the first and second needles 42 and 12 is started, a voltage differential is applied between the anode assemblies 91 and the first needle 42 which forms a cathode. The coil 94 is energized by the solenoid control 98 to move the tip 48 of the magnetic rod 96 inwards towards the outer surface of the first needle 42 until a glow discharge is initiated. The glow discharge is initiated when an appropriate current is achieved in the electrical path from the voltage source 14 (shown only in FIG. 1).

More particularly, a current sensing means (I SENSE) 19 (connected as shown in FIG. 1) is coupled to the solenoid control 98. The current sensing means 19 senses the amount of current delivered to the sterilization device 90, and sends a control signal to the solenoid control 98 indicating the current being sensed. The solenoid control 98 reacts to predetermined values of the current sensed by the current sensing means 19 to adjust the gap 13 between the tip 48 of the rod 96 and the first or second needle 42 or 1 accordingly. Therefore, as shown in FIG. 2, the current to the sterilization device 90 indicates, for example, when a glow discharge is initiated, etc. to start the sterilization of the first needle 42.

Once the glow discharge is initiated, the inward motion of the magnetic rod 96 is stopped, and the tip 48 of the rod 96 is retracted outwards from the surface of the first needle 42 until a predetermined current flow is obtained or sensed between the anode assemblies 91 and the first needle 42 (cathode) by the solenoid control 98. The predetermined current flow is a value which maintain the glow discharges at each of the gaps 13 between the tips 48 of the anode assemblies 91 and the first needle 42 in the manner shown in FIG. 2.

Once a desired length and an end of the first needle 42 is sterilized, the exposed portion of the second needle 12 is then sterilized once the end of the first needle has passed the tips 48 of the anode assemblies 91. More particularly, the gap 13 changes as the end of the first needle 42 passes the tips 48 of the anode assemblies 91 and the outer surface of the second needle 12 is exposed to the tips 48. This change in the gap 13 causes a slight change in the current through the gaps 13 which is corrected by the current solenoid control 98 via the current sensing means 19. In response to such change in current, the solenoid control 98 causes the tips 48 of the magnetic rods 96 to move towards the second needle 12. Such movement of the tips 48 towards the second needle 12 changes the gaps 13 to achieve a length between the tips 48 and the outer surface of the second needle 12 which produces substantially the same current as was previously encountered with the gaps 13 between the tips 48 and the outer surface of the first needle 42. In this manner the glow discharges are transferred from the first needle 42 to the second needle 12 without interruption. Therefore, sterilization device 90 provides an arrangement which adjusts to changes in shape of any irregularly shaped medical device.

It is to be appreciated and understood that the specific embodiments of the invention described hereinabove are merely illustrative of the general principles of the invention. Various modifications may be made by those skilled in the art which are consistent with the principles set forth. For example, the sterilization device 40 of FIG. 4 can be modified to sterilize any medical device such as injection needles, dental burrs, surgical knives, eye pressure measuring devices, etc. that have a substantially regular or irregular shape and are used for human or other use. Still further, an optional chamber 21 (as shown in FIG. 1) may be placed around the sterilizing devices 40, 60, 70, 80, and 90 of FIGS. 4, 6, 7, 8, and 9, respectively, to provide a predetermined gas at a predetermined pressure in the area of the projections 11 and the medical device 12, and/or collect products resulting from the glow discharge sterilization process. Additionally, in the device 10 of FIG. 1, the medical device 12 can be rotated while sequentially timed overlapping glow discharges 20 are produced to sterilize an entire area around the medical device 12. A predetermined length of the medical device 12 can also be sterilized by rotating the medical device 12 while concurrently moving the medical device 12 along longitudinal axis 18 to helically form overlapping glow discharges around and along the medical device 12. It is to be understood that the sterilization devices 40, 60, 70, 80, and 90 of FIGS. 4, 6, 7, 8, and 9, respectively, can be operated using an appropriate A.C. voltage source (not shown) that is suitable for forming the glow discharges 20 (only shown in FIG. 1), instead of using the D.C. voltage source 14 shown in FIG. 1.

What is claim is:

1. Apparatus for sterilizing an electrically conductive portion of a medical device comprising:

an electrode; and means for positioning the electrode a predetermined distance from the electrically conductive portion of the medical device, the electrode and the conductive portion of the medical device being separated by a gap which is sufficient, with an appropriate potential difference applied between the electrode and the medical device, to facilitate an electrical path between the electrode and the medical device so as to produce a glow discharge adjacent the outer surface of the medical device such that the portion of the medical device contacted by the glow discharge is sterilized.

2. The apparatus of claim 1 further comprising means for moving the medical device and the electrode relative to each other so that overlapping glow discharges are formed along a predetermined section of the medical device whereby the predetermined section of the medical device is sterilized.

3. The apparatus of claim 2 wherein a predetermined area of the medical device is locally heat sterilized by remaining stationary relative to the electrode while the glow discharge is continuously produced adjacent the predetermined area of the medical device for a predetermined time period to raise a local area of the medical device to a predetermined temperature.

4. Sterilizing apparatus comprising:

supporting means for supporting a medical device along a section to be sterilized, and for selectively applying a predetermined first voltage to the medical device; and an electrode comprising an anode tip which is arranged to provide a gap of a predetermined length between an outer surface of the medical device and the anode tip when the anode tip is positioned next to the medical device, and the electrode is arranged for selectively receiving a predetermined second voltage to provide a predetermined voltage differential across the gap so as to form a glow discharge adjacent the outer surface of the medical device in the area of the gap for sterilizing the outer surface of the medical device in the area of the glow discharge.

5. The sterilizing apparatus of claim 4 further comprising a plurality of electrodes which are positioned at substantially equal angular distances around the holding means and the medical device in a cross-sectional plane of the medical device, each electrode having an anode tip which is arranged to provide a gap of a predetermined length between a separate portion of the outer surface of the medical device and the anode tip when the anode tip is positioned next to the medical device so that a glow discharge produced by each electrode adjacent the outer surface of the medical device overlaps the glow discharge produced by each of the other electrodes on either side of the electrode, and all of the glow discharges form a continuous band of glow discharges around the outer surface of the medical device.

6. The sterilizing apparatus of claim 5 wherein a predetermined area of the medical device is further locally heat sterilized by remaining stationary relative to the plurality of electrodes while the glow discharges are continuously produced adjacent the predetermined area of the medical device for a predetermined time period to raise a local area of the medical device to a predetermined temperature.

7. The sterilizing apparatus of claim 5 further comprising:

means for moving the medical device in the supporting means and the plurality of electrodes relative to each other at a predetermined speed while maintaining the gap at each electrode substantially constant; and means for cyclically forming a sequence of glow discharges at predetermined time periods at each electrode of the plurality of electrodes such that each glow discharge formed by each electrode overlaps the previous glow discharge formed by the same electrode along a predetermined portion of the length of the medical device as the medical device and the plurality of electrodes are moved relative to each other.

8. The sterilizing apparatus of claim 5 wherein each of the plurality of electrodes is formed from an electrically conductive material, is flexible, and comprises an electrically insulating spacer having a predetermined width that is arranged to ride over an outer surface of the medical device for maintaining the gap at the predetermined length when the medical device is moved relative to the electrode.

9. The sterilizing apparatus of claim 5 wherein the medical device comprises a first and a second injection needle which are used to inoculate eggs wherein the first needle comprises a longitudinal aperture therethrough and is movable past the electrode to form an aperture in a shell of an egg, and the second needle rides within the longitudinal aperture of the first needle and into an interior of the egg to introduce a predetermined fluid therein.

10. The sterilizing apparatus of claim 9 wherein either one or both of the first and second needles are sterilized by glow discharges produced in the area of the anode tip of the electrode as the needles are withdrawn from contact with the egg.

11. The sterilizing apparatus of claim 9 wherein the first and second needles are disposed at a predetermined angle to each other from a point on the shell of the egg which is to be injected.

12. The sterilizing apparatus of claim 4 wherein the electrode is formed from an electrically conductive material, is flexible, and comprises an electrically insulating spacer having a predetermined width that is arranged to ride over the outer surface of the medical device for maintaining the gap at the predetermined length when the medical device and the electrode are moved relative to each other.

13. The sterilizing apparatus of claim 4 further comprising:

means for moving the medical device and the electrode relative to each other at a predetermined speed while maintaining the gap at the anode tip of the electrode substantially constant; and means for cyclically forming a sequence of glow discharges at predetermined time periods in an area of the anode tip of the electrode such that each glow discharge formed by the electrode overlaps the previous glow discharge formed by the electrode along a predetermined portion of the length of the outer surface of the medical device as the medical device and the electrode are moved relative to each other.

14. The sterilizing apparatus of claim 4 wherein the medical device comprises a first and a second injection needle which are used to inoculate eggs wherein the first needle comprises a longitudinal aperture therethrough and is movable past the electrode to form an aperture in a shell of an egg, and the second needle rides within the longitudinal aperture of the first needle and into an interior of the egg to introduce a predetermined fluid.

15. The sterilizing apparatus of claim 14 wherein either one or both of the first and second needles are sterilized by glow discharges produced in the area of the anode tip of the electrode as the needles are withdrawn from contact with the egg.

16. The sterilizing apparatus of claim 4 wherein the medical device has an irregular outer surface along a length to be sterilized, and the electrode further comprises means for selectively moving the anode tip in a plane substantially perpendicular to the length of the medical device so as to provide a gap of a substantially same predetermined length between an outer surface of the medical device and the anode tip to support a glow discharge as the irregular outer surface of the medical device is moved by the anode tip.

17. A method for sterilizing medical devices comprising the steps of:

(a) supporting a medical device along a section to be sterilized;

(b) selectively placing a portion of the medical device to be sterilized adjacent a anode tip of a electrode, the anode tip being arranged to provide a gap of a predetermined length between a separate portion of an outer surface of the medical device and the anode tip when the anode tip is positioned next to the medical device; and (c) selectively applying a sufficient potential difference between the anode tip of the electrode and the medical device to form a glow discharge in the area of the gap adjacent the outer surface of the medical device for sterilizing the outer surface of the medical device in the area of the glow discharge.

18. The method of claim 17 wherein:

in performing step (b), selectively placing the portion of the medical device to be sterilized adjacent a plurality of electrodes which are positioned at substantially equal angular distances around the medical device in a cross-sectional plane of the medical device, each electrode having a anode tip which is arranged to provide a gap of a predetermined length between a separate portion of the outer surface of the medical device and the anode tip when the anode tip is positioned next to the medical device; and in performing step (c), selectively applying a sufficient potential difference between each of the plurality of electrodes and the medical device so that a glow discharge is produced by each electrode adjacent the outer surface of the medical device which overlaps the glow discharge produced by each of the other electrodes on either side of the electrode, and all of the glow discharges form a continuous band of glow discharges around the outer surface of the medical device.

19. The method of claim 18 comprising the further steps of:

(d) moving the medical device and the plurality of electrodes relative to each other at a predetermined speed while maintaining the gap at each electrode substantially constant; and (e) cyclically forming a sequence of glow discharges at predetermined time periods at each electrode of the plurality of electrodes such that each glow discharge formed by each electrode overlaps the previous glow discharge formed by the same electrode along a predetermined portion of the length of the medical device as the medical device and the plurality of electrodes are moved relative to each other.

20. The method of claim 18 wherein in step (c) selectively applying the sufficient potential difference between each of the electrodes and the medical device to form continuous glow discharges while maintaining the medical device at a predetermined stationary position relative to the plurality of electrodes for heating a localized area of the medical device to a predetermined temperature.

21. The method of claim 18 wherein each of the plurality of electrodes is formed from an electrically conductive material, is flexible, and comprises an electrically insulating spacer having a predetermined width that is arranged to ride over an outer surface of the medical device for maintaining the gap at the predetermined length when the medical device is moved relative to the electrode.

22. The method of claim 18 wherein the medical device comprises first and second injection needles which are used to inoculate eggs wherein the first needle comprises a longitudinal aperture therethrough, and in step (b) performing the substeps of:

(b1) selectively moving the first needle past the electrode to form an aperture in a shell of an egg; and (b2) selectively moving the second needle within the longitudinal aperture of the first needle and into an interior of the egg to introduce a predetermined fluid therein.

23. The method of claim 22 wherein the first and second needles are disposed at a predetermined angle to each other from a point on the shell of the egg which is to be injected.

24. The method of claim 22 wherein in performing step (c), selectively applying a sufficient potential difference between each of the plurality of electrodes and the medical device for sterilizing either one or both of the first and second needles by glow discharges produced in the area of the anode tip of the electrodes as the needles are withdrawn from contact with the egg.

25. The method of claim 17 wherein the electrode is formed from an electrically conductive material, is flexible, and comprises an electrically insulating spacer having a predetermined width that is arranged to ride over the outer surface of the medical device for maintaining the gap at the predetermined length when the medical device and the electrode are moved relative to each other.

26. The method of claim 17 further comprising the steps of:

(d) moving the medical device and the electrode relative to each other at a predetermined speed while maintaining the gap at the anode tip of the electrode substantially constant; and (e) cyclically forming a sequence of glow discharges at predetermined time periods in an area of the anode tip of the electrode such that each glow discharge formed by the electrode overlaps the previous glow discharge formed by the electrode along a predetermined portion of the length of the outer surface of the medical device as the medical device and the electrode are moved relative to each other.

27. The method of claim 17 wherein the medical device comprises a first and a second injection needle which are used to inoculate eggs wherein the first needle comprises a longitudinal aperture therethrough, and in step (b) performing the substeps of:

(b1) selectively moving the first needle past the electrode to form an aperture in a shell of an egg; and (b2) selectively moving the second needle within the longitudinal aperture of the first needle and into an interior of the egg to introduce a predetermined fluid therein.

28. The method of claim 27 wherein in performing step (c), selectively applying a a sufficient potential difference between each of the plurality of electrodes and the medical device for sterilizing one or both of the first and second needles by glow discharges produced in the area of the anode tip of the electrodes as the needles are withdrawn from contact with the egg.

29. The method of claim 17 wherein the medical device has an irregular outer surface along a length to be sterilized, and in performing steps (b) and (c), selectively moving the anode tip in a plane substantially perpendicular to the length of the medical device so as to provide a gap of a substantially same predetermined length between an outer surface of the medical device and the anode tip to support a glow discharge as the irregular outer surface of the medical device is moved by the anode tip.

* * * * *